(12) United States Patent
Hollingsworth

(10) Patent No.: US 7,498,430 B2
(45) Date of Patent: Mar. 3, 2009

(54) PROCESS FOR THE PREPARATION AND SEPARATION OF ARABINOSE AND XYLOSE FROM A MIXTURE OF SACCHARIDES

(75) Inventor: Rawle I. Hollingsworth, Haslett, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 529 days.

(21) Appl. No.: 10/984,529

(22) Filed: Nov. 9, 2004

(65) Prior Publication Data

US 2006/0100423 A1    May 11, 2006

(51) Int. Cl.
*C07H 1/06* (2006.01)
*C07H 1/08* (2006.01)
(52) U.S. Cl. ...................... 536/127; 536/128
(58) Field of Classification Search ........................ None
See application file for complete search history.

(56) References Cited

U.S. PATENT DOCUMENTS

| | | | |
|---|---|---|---|
| 5,917,059 A | 6/1999 | Bruchmann et al. | |
| 6,451,123 B1 * | 9/2002 | Saska et al. | 127/46.2 |
| 6,548,681 B1 | 4/2003 | Chopade et al. | |
| 6,713,640 B2 | 3/2004 | Miller et al. | |

OTHER PUBLICATIONS

Lawson. Sugar Alcohols, Kirt-Othmer Encyclopedia of Chemical Technology, 1997 by John Wily & Sons, Inc.*
Swamy et al. Tetrahedron Letters 43 (2002) 7549-7552.*

* cited by examiner

*Primary Examiner*—Shaojia Anna Jiang
*Assistant Examiner*—Layla Bland
(74) *Attorney, Agent, or Firm*—Ian C. McLeod

(57) ABSTRACT

A process for the preparation and separation of the pentoses, xylose and arabinose from mixtures of saccharides by forming acetals is described. D-xylose is a precursor to xylitol, a sweetener, and L-arabinose is a precursor to the drug intermediate (R)-3,4-dihydroxybutyric acid, carnitine and agrichemicals.

10 Claims, 18 Drawing Sheets

PROCESS FOR THE PREPARATION AND SEPARATION OF ARABINOSE AND XYLOSE FROM A MIXTURE OF SACCHARIDES

CROSS-REFERENCE TO RELATED APPLICATIONS

Not Applicable

STATEMENT REGARDING FEDERALLY SPONSORED RESEARCH OR DEVELOPMENT

Not Applicable

STATEMENT REGARDING GOVERNMENT RIGHTS

Not Applicable

BACKGROUND OF THE INVENTION (1) Field of the Invention

The present invention relates to the formation of sugar acetals or ketals as a means for the separation of the pentoses, xylose and arabinose from mixtures of saccharides. In particular, the present invention relates to the separation of the pentoses from lignocellulosic materials which have been hydrolyzed. The present invention further relates to the separation of xylose and arabinose from each other and to the selective recovery of arabinose from a mixture of monosaccharides, oligosaccharides and polysaccharides.

(2) Description of the Related Art

The batch and continuous recovery of cyclic acetals or ketals of polyols without a heterocyclic ring structure by distillation of mixtures of acetals or ketals is illustrated by U.S. Pat. No. 5,917,059 to Bruchmann et al and U.S. Pat. Nos. 6,548,681 B1 and 6,713,640 B2 to Miller et al. These processes are relatively straight forward but do not involve pentose isomers.

There is a need for a simpler and more economic process for producing the pentoses, xylose and arabinose, particularly from natural cellulosic sources. While the sugars can be digested with enzymes, the separation of the resulting monosaccharides is a problem which needs to be solved.

OBJECTS

It is therefore an object of the present invention to provide a process for the recovery and separation of pentoses from a complex mixture of. Further it is an object of the present invention to provide a process which is economical and thus yields the separated monosaccharides at a reasonable cost. These and other objects will become increasingly apparent by reference to the following description.

SUMMARY OF THE INVENTION

The present invention relates to a process for the separation of arabinose and xylose acetals from a mixture comprised of saccharides particularly monosaccharides, oligosaccharides and/or polysaccharides which comprises: reacting the mixture with a ketone or aldehyde so as to form acetals of the monosaccharides; and separating the arabinose and xylose acetals from the reaction mixture by a solvent extraction, by distillation, or chromatography.

The present invention also particularly relates to a process for the separation of arabinose and xylose acetals from a mixture comprised of saccharides particularly monosaccharides, oligosaccharides and/or polysaccharides which comprises: reacting the mixture with a ketone or aldehyde so as to form the acetals of the saccharides; concentrating the mixture to a syrup; extracting the syrup with a non-polar organic solvent in which the acetals of the other saccharides binds the acetals of arabinose and xylose are insoluble to provide the acetals of arabinose and xylose in the organic solvent; and separating the arabinose, xylose acetals from the organic solvent. Under specific conditions, the diacetal of arabinose only can be formed to allow this pentose to be recovered selectively from a mixture of monosaccharides, oligosaccharides and/or polysaccharides by extraction with a suitable non-polar solvent.

Preferably the mixture is from a hydrolysate of corn fiber or sugar beet pulp. Preferably the arabinose acetal and xylose acetal are separated from each other by selective removal of the 3,5-acetal group of xylose followed by solvent partitioning using water and an organic non-polar solvent, distillation or chromatography.

In the process illustrated in FIG. 1, L-arabinose and D-xylose are recovered from complex carbohydrate matrices such as corn fiber and sugar beet pulp. Standard methods for the release of these sugars from the lignocellulose are used. These include treatment with acid in aqueous solution at room temperature or at elevated temperatures. Before acid hydrolysis, corn fiber or sugar beet pulp are pre-treated with hot water to extract the vast majority of the lignocellulosic material which contains the pentose sugars. In a refinery setting, the residue, which is largely cellulose, is digested by enzymes for the production of the glucose carbon source used by microorganisms for lactic acid production. There is a need to recover the pentose sugars.

Preferably mixture of the pentose sugars from the enzymatic treatment of the lignocellulose was dried and treated with acetone or other ketone or aldehyde in the presence of acid. The use of an acyclic acetal such as 2,2-dimethoxypropane aids acetalization by preventing hydrolysis of the acetal or ketal. Water scavengers such as orthoesters can also be added to aid the acetalization. After neutralization with an organic or inorganic base, the solvents were removed and the mixture was extracted with hexane or other hydrocarbon solvent. The extract contains the diacetals of L-arabinose (1) and D-xylose (2). Alternatively, the diacetals can be extracted with a non-polar supercritical solvent such as carbon dioxide or they can be recovered together by distillation from the mixture. The polarity of the solvent needs to be low enough that any acetals of hexose sugars, oligosaccharides or polysaccharides are not extracted. The mixture of diacetals was treated in a polar solvent such as methanol or water under conditions that react only the 3,5-acetal group of D-xylose to give a 3,5-diol of xylose. The mixture was then neutralized with base and an immiscible (non-polar) solvent was added. The layers were separated to give the individual protected pentoses. The acetals were deprotected by acid hydrolysis to give the pentoses, xylose and arabinose. Xylose is formed as a five 95) membered ring from the acetal protected D-xylofuranose.

Xylose is important for the preparation of xylitol which is used as a sugar replacement for sweetening in many food applications. It is also a valuable starting material for chemistry applications. L-Arabinose is also an important material. It is one of the very few L-sugars found in significant amounts. It is an important starting material for the production of (R)-3,4-dihydroxybutyric acid an important intermediate used for the preparation of pharmaceuticals, agrichemicals, carnitine and materials.

DESCRIPTION OF PREFERRED EMBODIMENTS

Based upon the following Examples 1 to 11, it was found that:

(1) Acetalization and separation can be used to recover xylose and arabinose from mixtures of hexose sugars, oligosaccharides and polysaccharides.

(2) The 1,2-3,4-diacetal of L-arabinose and the 1,2-3,5 diacetal of D-xylose can both be recovered by extraction with hexane, toluene, dichloromethane or other non-polar solvent. Non-polar solvents include the alkanes and vegetable oils. Selective recovery to exclude other acetals such as hexose acetals and acetals of oligosaccharides and polysaccharides that have one or more hydroxyl groups can be accomplished by extraction with hexane, pentane and other hydrocarbon solvents.

(3) The 1,2-3,4-diacetal of L-arabinose and the 1,2-3,5 diacetal of D-xylose can both be recovered by distillation under reduced temperature at steam temperatures. Again other acetals such as hexose acetals and acetals of oligosaccharides and polysaccharides that have one or more hydroxyl groups are not volatile under these conditions. 1

(4) The 3,5-acetal group of the xylose diacetal can be removed selectively under acid hydrolysis conditions without disturbing the other acetal groups of both sugars enabling separation of the two pentoses.

(5) The 1,2-xylose monoacetal can be separated from the 1,2-3,4-di-arabinose acetal by solvent partitioning between a polar and a non-polar solvent.

(6) The 1,2-xylose monoacetal can be separated from the 1,2-3,4-di-arabinose acetal by distilling away the volatile diacetal.

(7) The 1,2-xylose monoacetal can be separated from the 1,2-3,4-di-arabinose acetal by chromatography.

(8) The arabinose can be recovered selectively as the di-acetal from mixtures of the pentoses with hexoses, oligosaccharides and polysaccharides if dimethoxypropane is not added.

EXAMPLES 1 TO 3

Preparation of mixture of 1,2-3,4-di-O-isopropylidene-L-arabinopyranose and 1,2-3,5-di-O-isopropylidene-D-xylofuranose

Example 1

Figure 1:
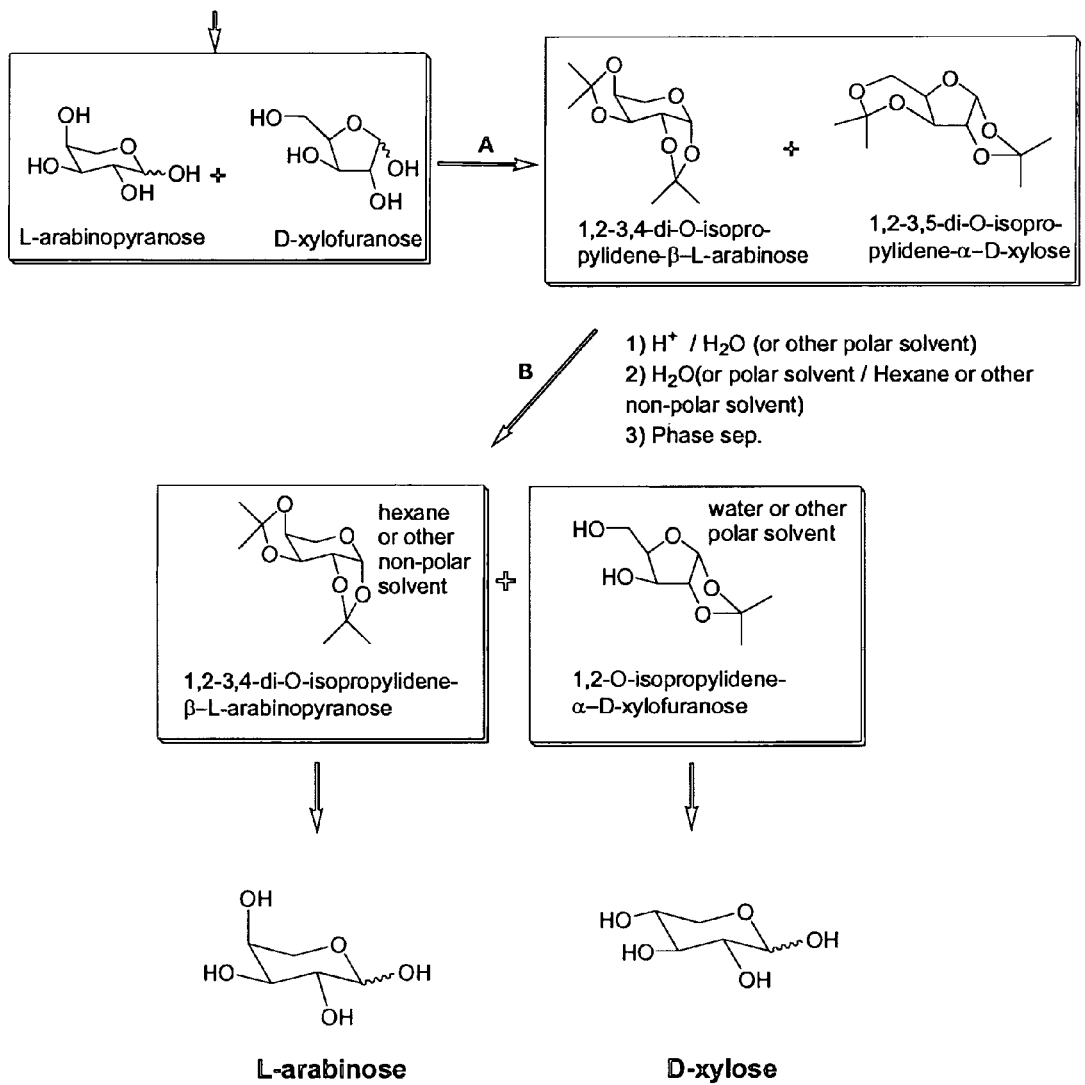
FIG. 1 is a schematic diagram of the preferred chemical process of the present invention.
Figure 2:
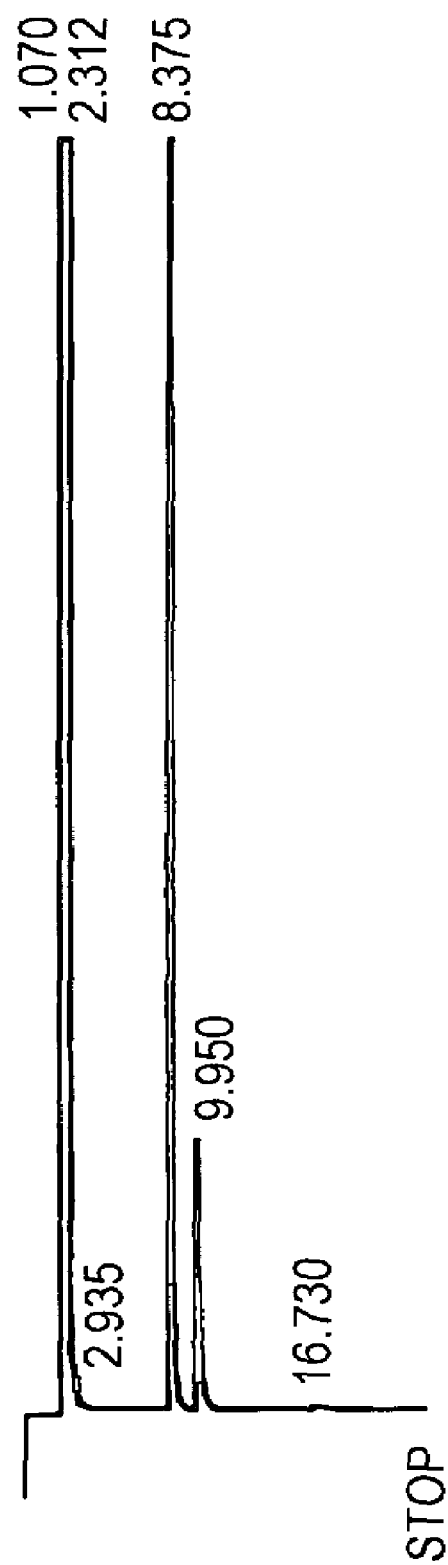
FIGS. 2 to 18 are Gas Chromatographs (GC) and $^1$H and $^{13}$C NMR spectroscopy of the products of Examples 1 to 11. Examples 1 to 3 Figures show preparation of a mixture of 1,2-3,4-di-O-isopropylidene-L-arabinopyranose and 1,2-3,5-di-O-isopropylidene-D-xylofuranose and the GCs and NMRs. Examples 4 and 5 show preparation of a mixture of 1,2-3,4-diO-isopropylideneL-arabinopyranose and 1,2-3,5-di-O-isopropylidene-D-xylofuranose and isolation from a mixture of arabinose, xylose, glucose and maltose and the GC in FIGS. 7 and 8. Example 6 shows preparation of selective hydrolysis of 1,2-3,5-di-O-isopropylidene-D-xylose to the 1,2-monoacetal in a mixture of 1,2-3,4-di-O-isopropylidene-L-arabinopyranose and 1,2-3,5-di-O-isopropylidene-D-xylofuranose and the GC. Example 7 shows preparation of selective hydrolysis of 1,2-3,5-di-O-isopropylidene-D-xylose to the 1,2-monoacetal in a mixture of 1,2-3,4-di-O-isopropylidene-L-arabinopyranose and 1,2-3,5-di-O-isopropylidene-D-xylofuranose and separation of the products and the Ge, (FIG. 11), $^1$H (FIG. 12) and $^{13}$C (FIG. 13). Example 9 shows preparation of recovery and separation of arabinose and xylose from complex carbohydrate polymers and the GC (FIG. 16). Example 10 shows preparation of recovery of arabinose and xylose from gum ghatti and the GC (FIG. 17). Example 11 shows preparation of recovery of arabinose and xylose from gum Arabic and the GC (FIG. 18).
Figure 3:
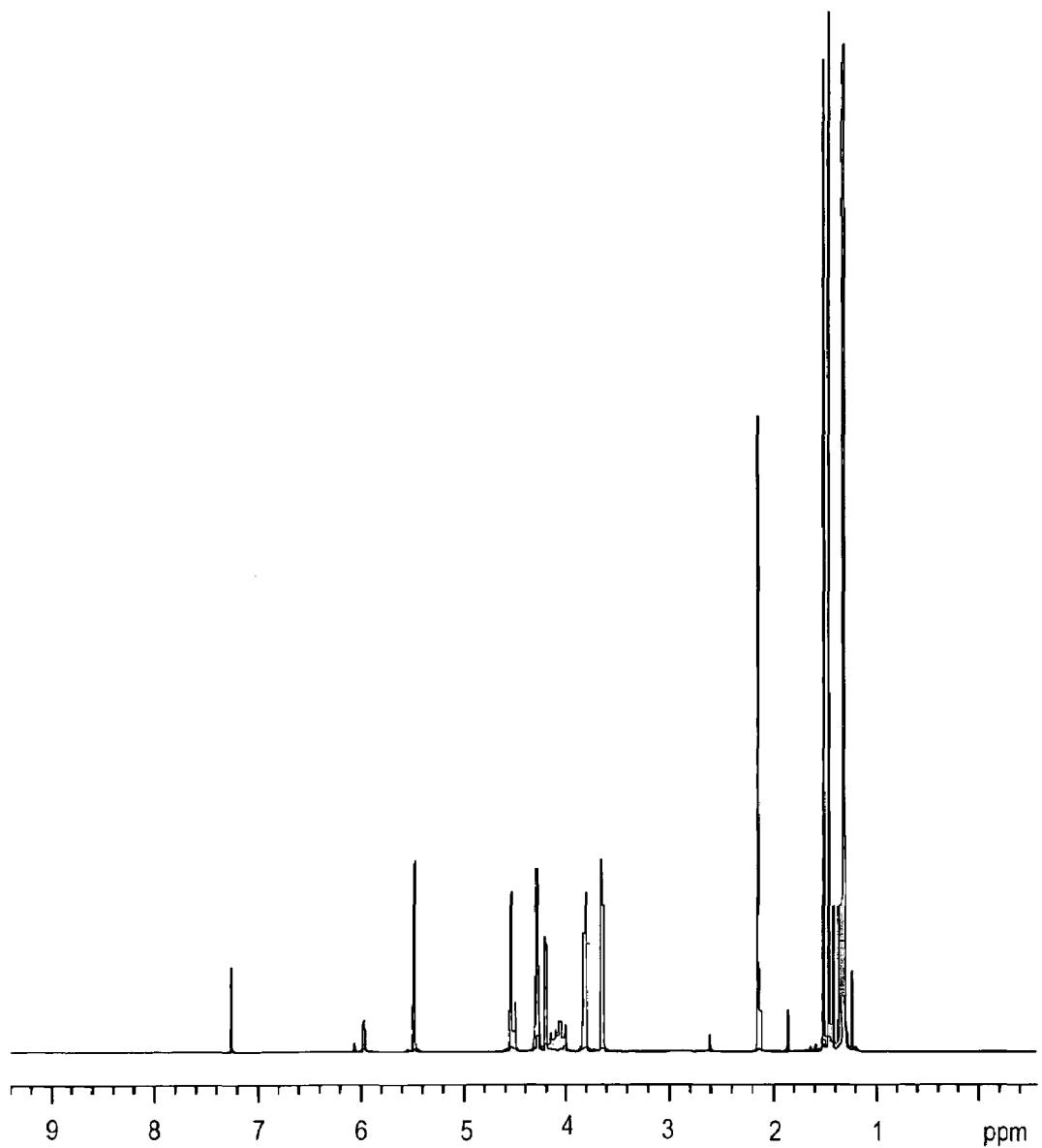
Figure 4:
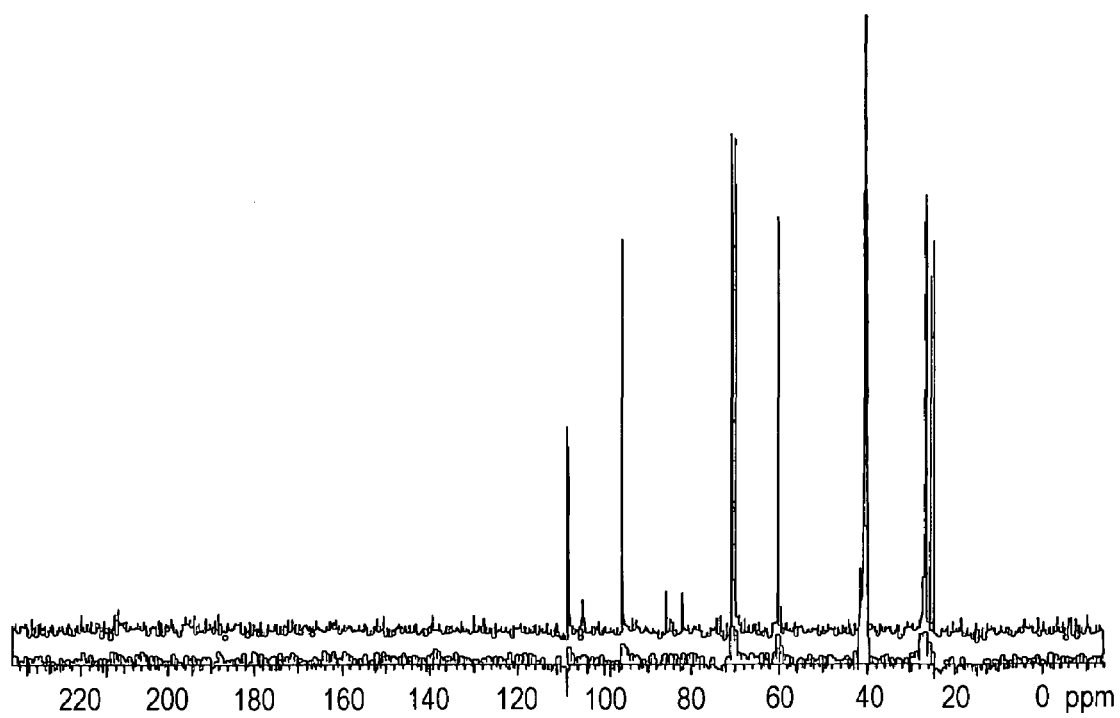

L-arabinose (18.6 g) and D-ribose (18.6 g) as powders were suspended in 1400 ml acetone and 4 ml sulfuric acid (98%) added. The mixture was stirred at room temperature for 14 hours and then potassium carbonate (12 g) was added to neutralize the solution. Stirring was continued for a further 2 hours and the mixture was filtered and concentrated to a syrup. The total yield was 37 grams (63%). The product mixture was analyzed by GC (FIG. 2) and $^1$H (FIG. 3) and $^{13}$C (FIG. 4) NMR spectroscopy. GC conditions were 120° to 220° at 5°/min. Final temp=220°. Final time=20 mins (30 meter DB225 column). Injection temp=220°, Detection temp=230°. The mixture contained 74% of the arabino acetal.

Example 2

Figure 5:
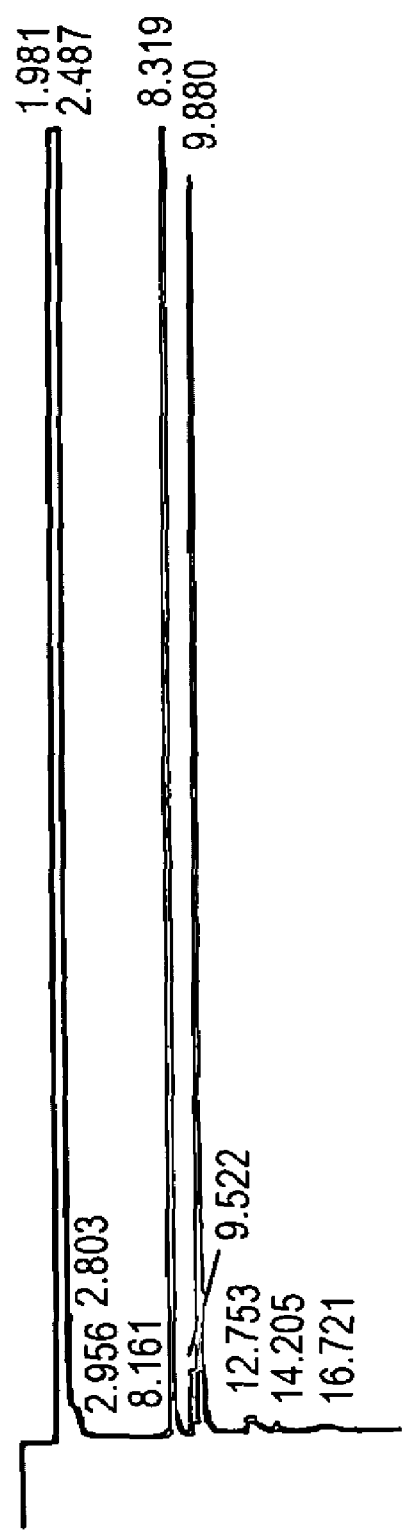
Figure 6:
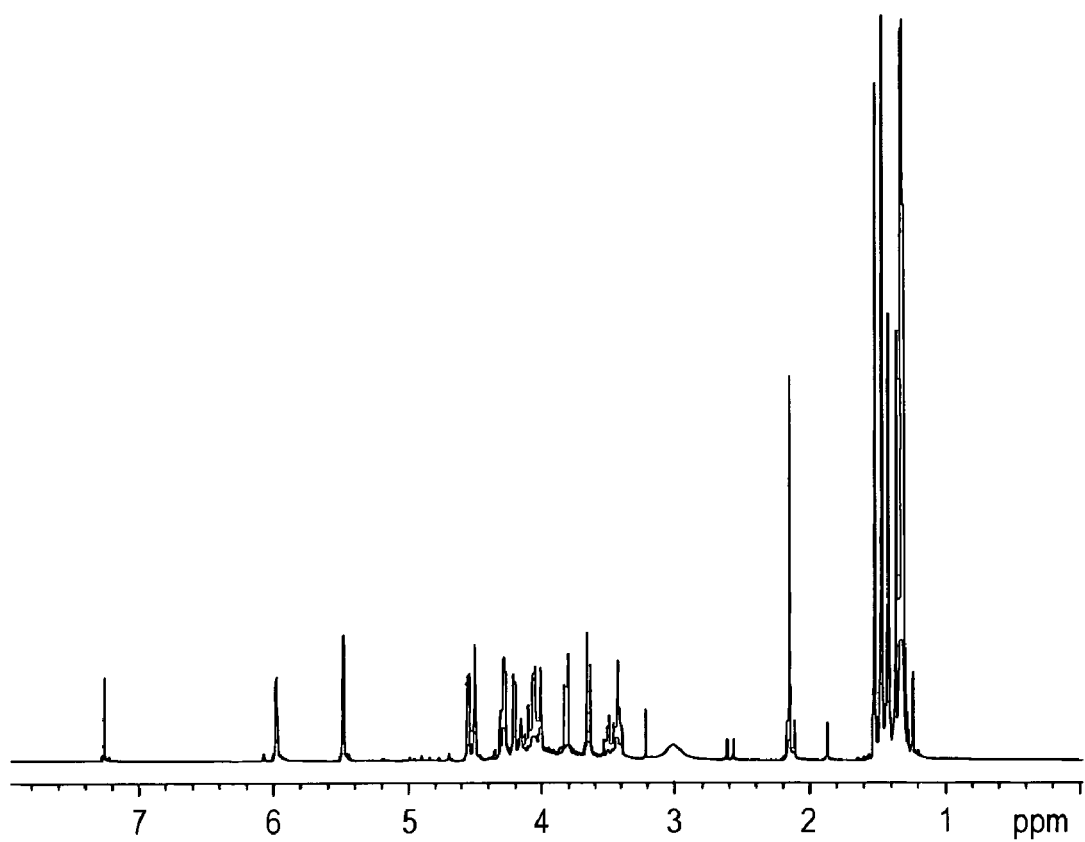
Figure 7:
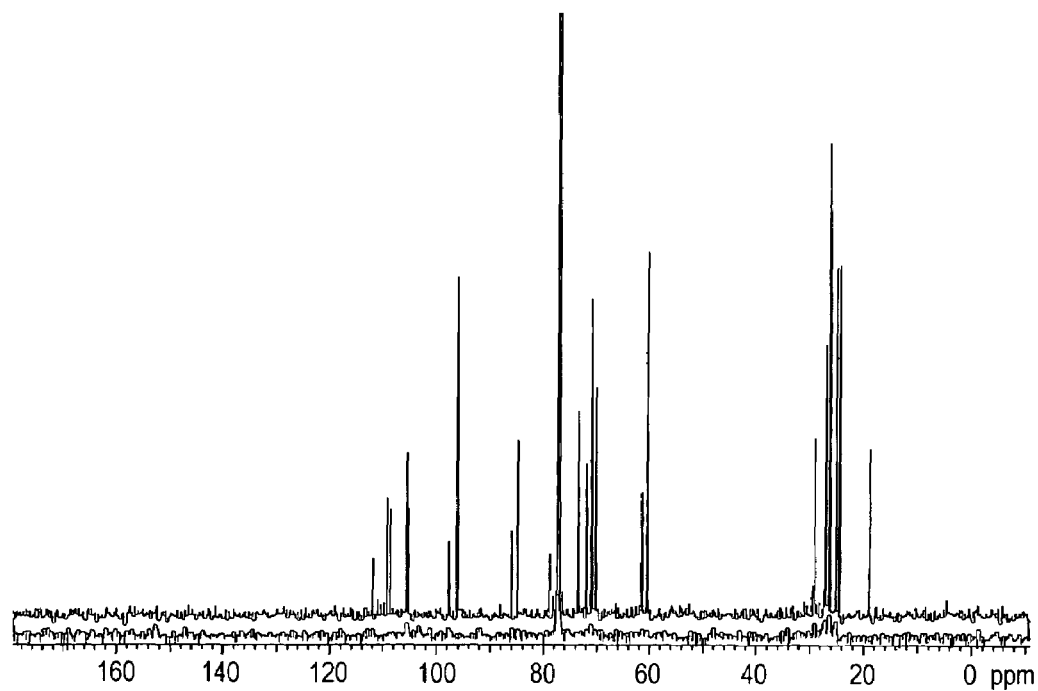

L-arabinose (18.6 g) and D-ribose (18.6 g) as powders were suspended in 1400 ml acetone and 4 ml sulfuric acid (98%) added. Dimethoxypropane (40 g) was then added to aid acetylation in contrast to Example 1. The mixture was stirred at room temperature for 14 hours and then potassium carbonate (12 g) was added to neutralize the solution. Stirring was continued for a further 2 hours and the mixture was filtered and concentrated to a syrup. The total yield was 53.8 grams (93%) which was higher than Example 1. The product mixture was analyzed by GC (FIG. 5) and $^1$H (FIG. 6) and $^{13}$C (FIG. 7) NMR spectroscopy.

Example 3

Distillation Separation

L-arabinose (18.6 g) and D-ribose (18.6 g) as powders were suspended in 1400 ml acetone and 4 ml sulfuric acid (98%) added. Dimethoxypropane (40 g) was then added as in Example 2. The mixture was stirred at room temperature for 14 hours and then potassium carbonate (12 g) was added. Stirring was continued for a further 2 hours and the mixture was filtered and concentrated to a syrup. The total yield was 52.1 grams (92%). The product mixture was distilled under reduced pressure and 3 fractions collected.
Fraction 1 (94-98°, 16 mm Hg), 9.5 grams
Fraction 2 (98-102°, 16 mm Hg), 12.4 grams
Fraction 3 (102-105°, 16 mm Hg), 10.0 grams

Examples 4 and 5

Preparation of mixture of 1,2-3,4-di-O-isopropylidene-L-arabinopyranose and 1,2-3,5-di-O-isopropylidene-D-xylofuranose and isolation from a mixture of arabinose, xylose, glucose and maltose

Example 4

Figure 8:
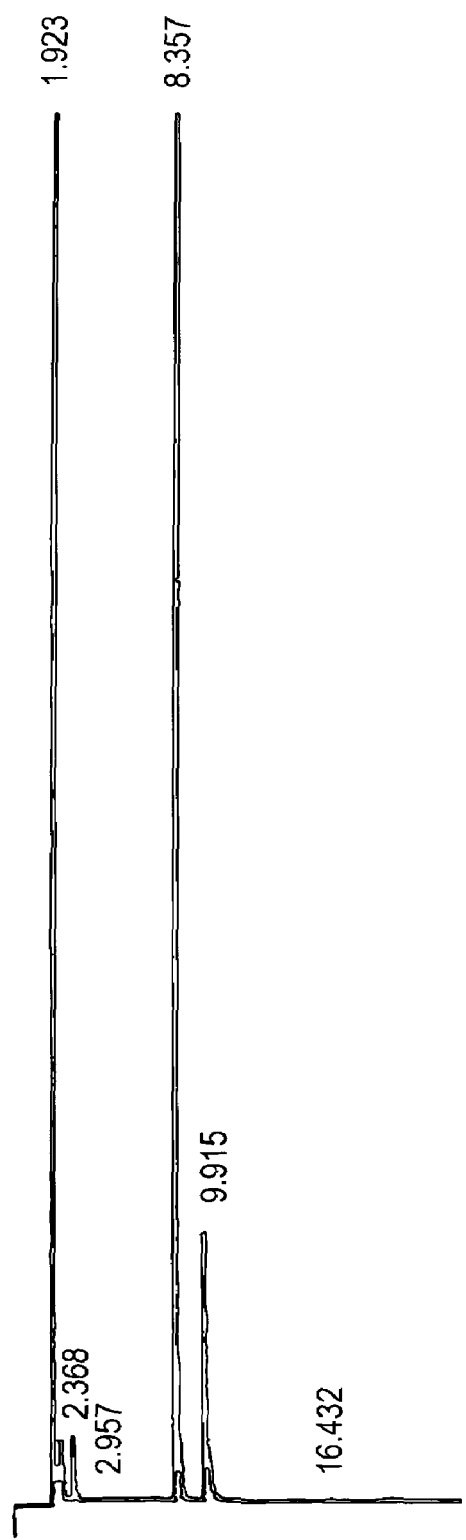
Figure 9:
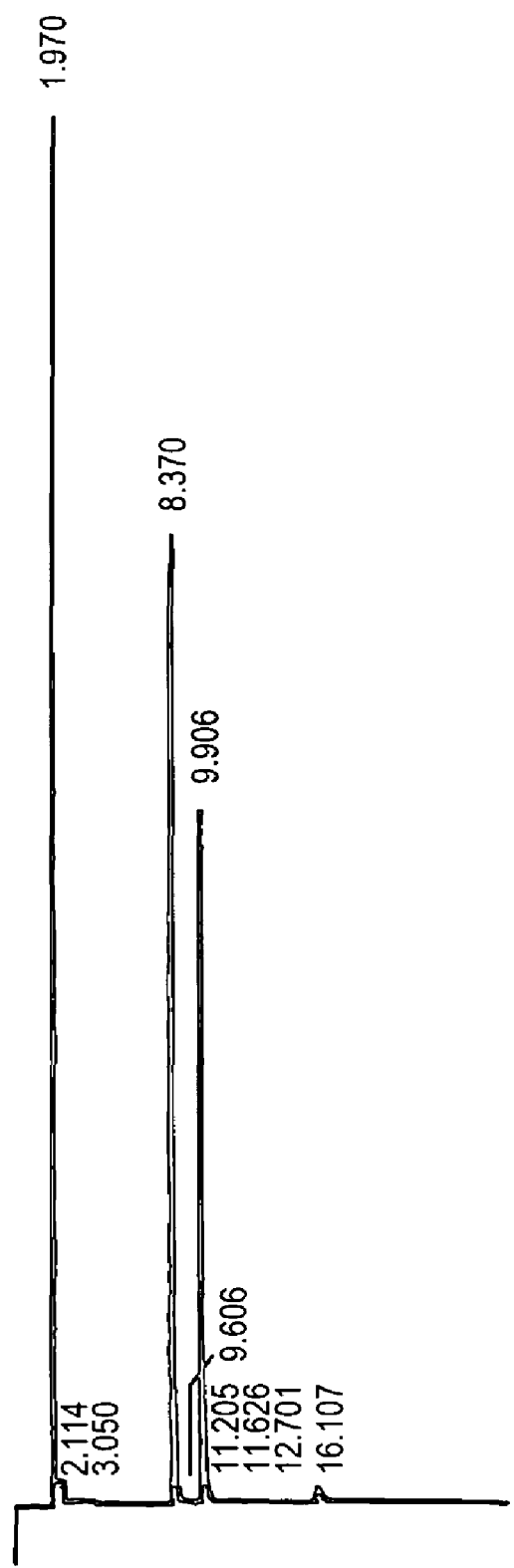

L-arabinose (5.0 g), D-ribose (5.0 g), D-glucose (5.0 g) as powders and maltose (5.0 g) were suspended in 500 ml acetone and 2 ml sulfuric acid (98%) added. The mixture was stirred at room temperature for 14 hours and then potassium carbonate (1.2 g) was added to neutralize the solution. Stirring was continued for a further 2 hours and the mixture was filtered and concentrated to a syrup. The total yield was 9.6 grams (63% yield). GC analyses (FIG. 8) indicated that the extract contained only 1,2-3,4-di-O-isopropylidene-L-arabinopyranose and 1,2-3,5-di-O-isopropylidene-D-xylofuranose in a 2.7:1 ratio (73% arabinose acetal).

Example 5

L-arabinose (5.0 g), D-ribose (5.0 g), D-glucose (5.0 g) as powders and maltose (5.0 g) were suspended in 500 ml acetone and 2 ml sulfuric acid (98%) added. Dimethoxypropane (10.0 g) was then added in contrast to Example 4. The mixture was stirred at room temperature for 14 hours and then potassium carbonate (1.2 g) was added to neutralize the solution. Stirring was continued for a further 2 hours and the mixture was filtered and concentrated to a syrup. The total yield was 14.0 grams (92% yield). GC analyses (FIG. 7) indicated that the extract contained only 1,2-3,4-di-O-isopropylidene-L-arabinopyranose and 1,2-3,5-di-O-isopropylidene-D-xylofuranose in the ratio of 1.4:1 (58%) arabinose acetal.

Example 6

Figure 10:
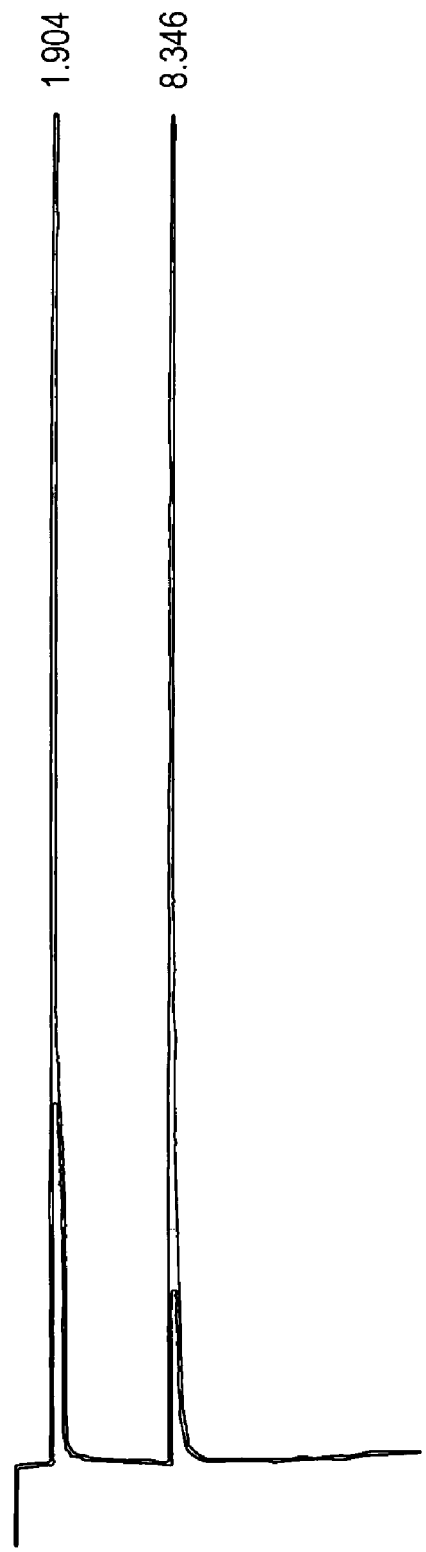

Selective hydrolysis of 1,2-3,5-di-O-isopropylidene-D-xylose to the 1,2-monoacetal in a mixture of 1,2-3,4-di-O-isopropylidene-L-arabinopyranose and 1,2-3,5-di-O-isopropylidene-D-xylofuranose Concentrated HCl (1 ml), water (1 ml) and methanol (20 ml) were mixed together. One hundred mg of a 1:1 acetal mixture was dissolved in 2 ml of the acidic methanol. After 25 mins 20 microliters of a 20% solution of sodium hydroxide was added to neutralize the solution. Hexane (4 ml) was then added. After brief mixing the layers were separated and the upper hexane layer was dried with sodium sulfate and analyzed by GC (FIG. 10) which indicated that all of the 1,2-3,5-di-O-isopropylidene-D-xylofuranose had been converted to the 1,2-monoacetal as a result of the selective hydrolysis.

Example 7

Figure 11:
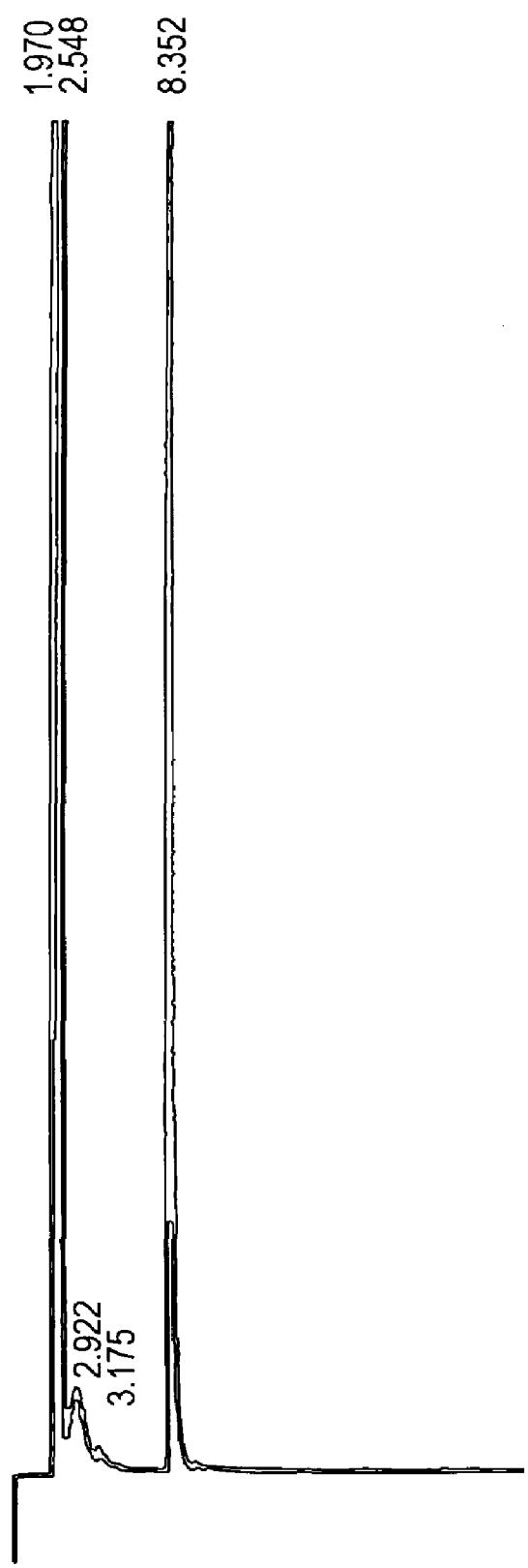
Figure 12:
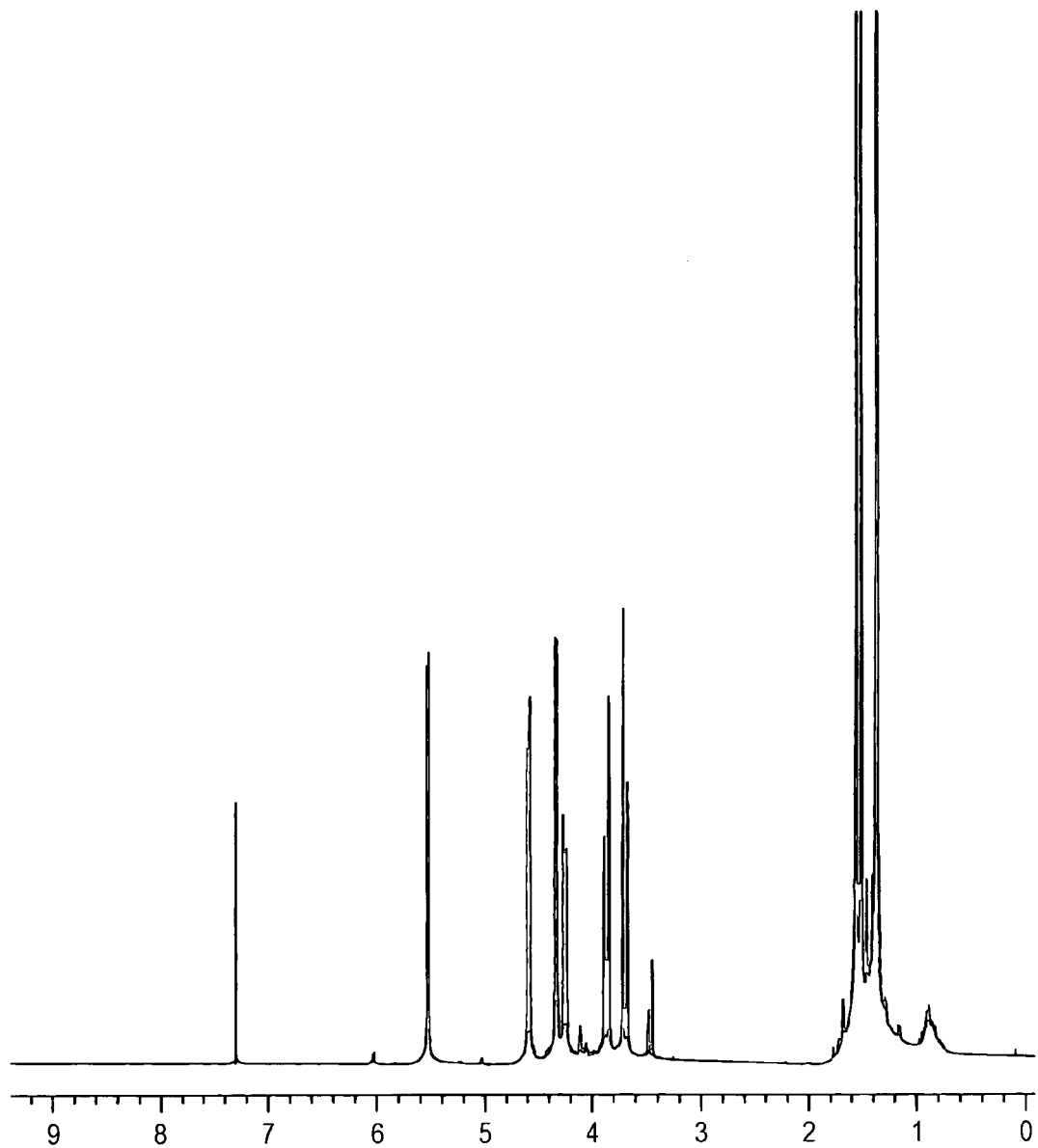
Figure 13:
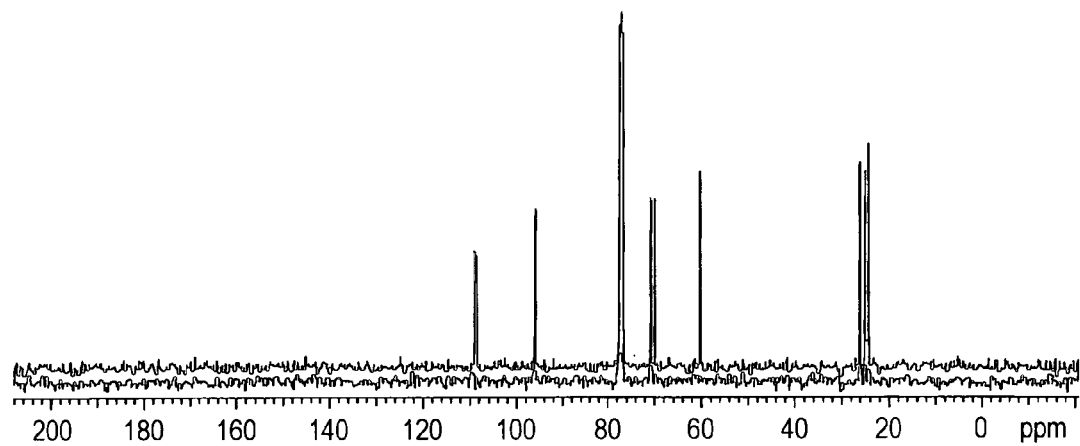
Figure 14:
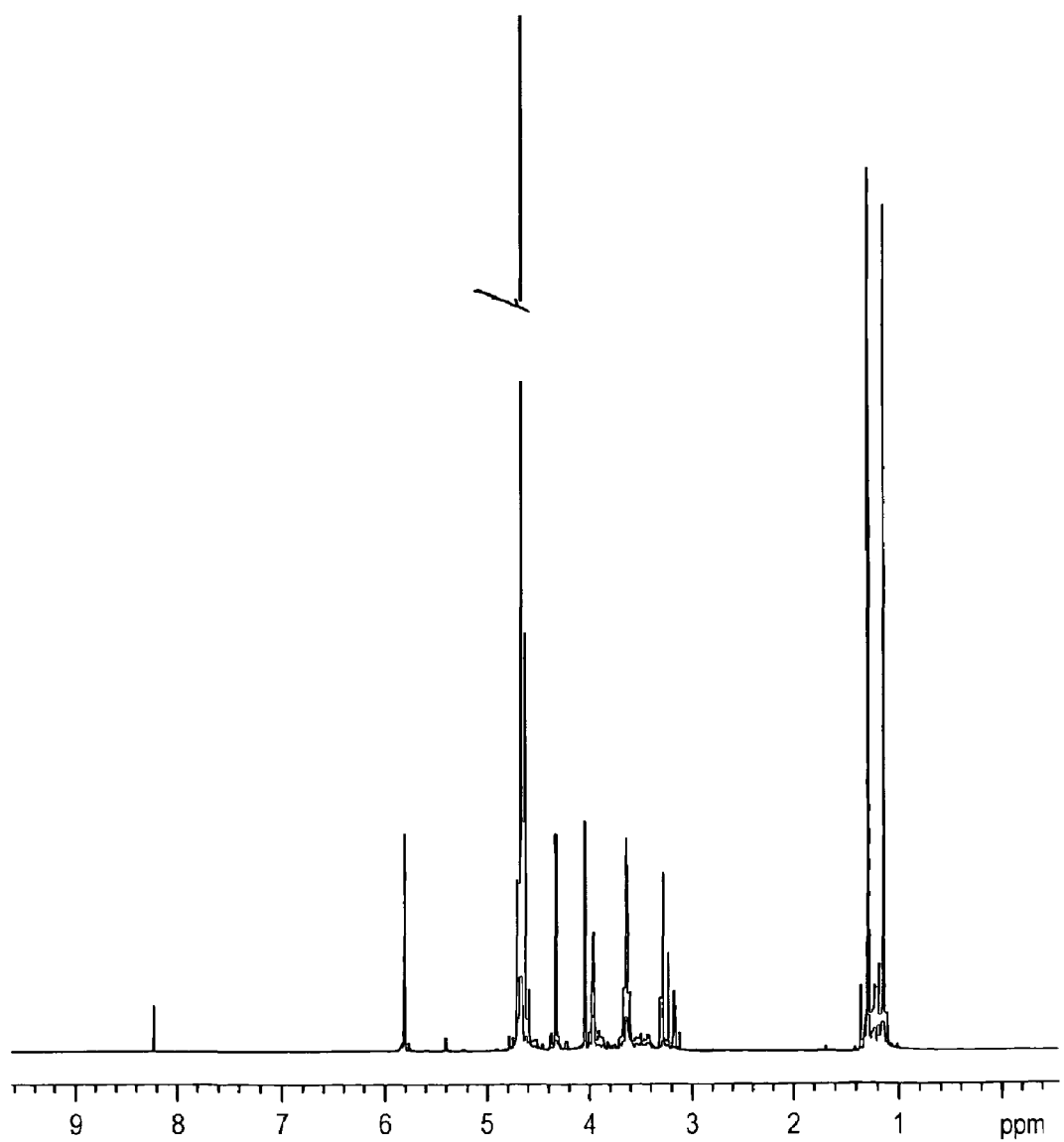
Figure 15:
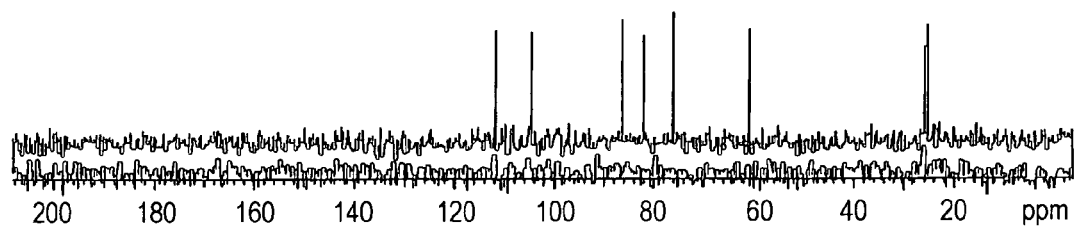

Selective hydrolysis of 1,2-3,5-di-O-isopropylidene-D-xylose to the 1,2-monoacetal in a mixture of 1,2-3,4-di-O-isopropylidene-L-arabinopyranose and 1,2-3,5-di-O-isopropylidene-D-xylofuranose and separation of the products Concentrated HCl (5 ml), water (5 ml) and methanol (100 ml) were mixed together. 24 grams of a 1:1 acetal mixture was dissolved in the acidic methanol solution. After 30 mins 20 ml of a 25% solution of sodium hydroxide was added to neutralize the solution. Hexane (400 ml) was then added. After brief mixing the layers were separated and the upper hexane layer was dried with sodium sulfate, concentrated and analyzed by GC (FIG. 11) and $^1$H (FIG. 12) and $^{13}$C (FIG. 13) NMR spectroscopy. GC analyses indicated that all of the 1,2-3,5-di-O-isopropylidene-D-xylofuranose had been converted to the 1,2-monoacetal and the layer was 99% arabino di-acetal. NMR analyses also indicated that exclusively arabino diacetal was present in the hexane layer. The yield was 12.1 grams (~100%). The lower layer was concentrated to give a crude yield of 29.30 grams. This was taken up in tetrahydrofuran and the THF solution dried (sodium sulfate) and concentrated to give 9.7 grams (98%) of the mono acetal. $^1$H (FIG. 14) and $^{13}$C (FIG. 15) NMR spectra indicated that this layer contained only the 1,2-monoacetal.

Example 8

Alternative separation procedure for products from selective hydrolysis of 1,2-3,5-di-O-isopropylidene-D-xylose to the 1,2-monoacetal in a mixture of 1,2-3,4-di-O-isopropylidene-L-arabinopyranose and 1,2-3,5-di-O-isopropylidene-D-xylofuranose A mixture of the neutralized hydrolysis products from the process described in Example 5 was distilled in a Kugelrohr distillation apparatus (Sigman Aldrich US) for temperature sensitive materials with a vacuum of 2-4 mm Hg and a temperature of 150-200 degrees centigrade and the 1,2-3,4-di-O-isopropylidene-L-arabinopyranose collected. No loss of the diacetal was observed. The residue was treated with decolorizing carbon and filtered. NMR analyses indicated that it was the 1,2-monoacetal essentially free of the diacetal. There was no evidence of degradation.

Example 9

Figure 16:
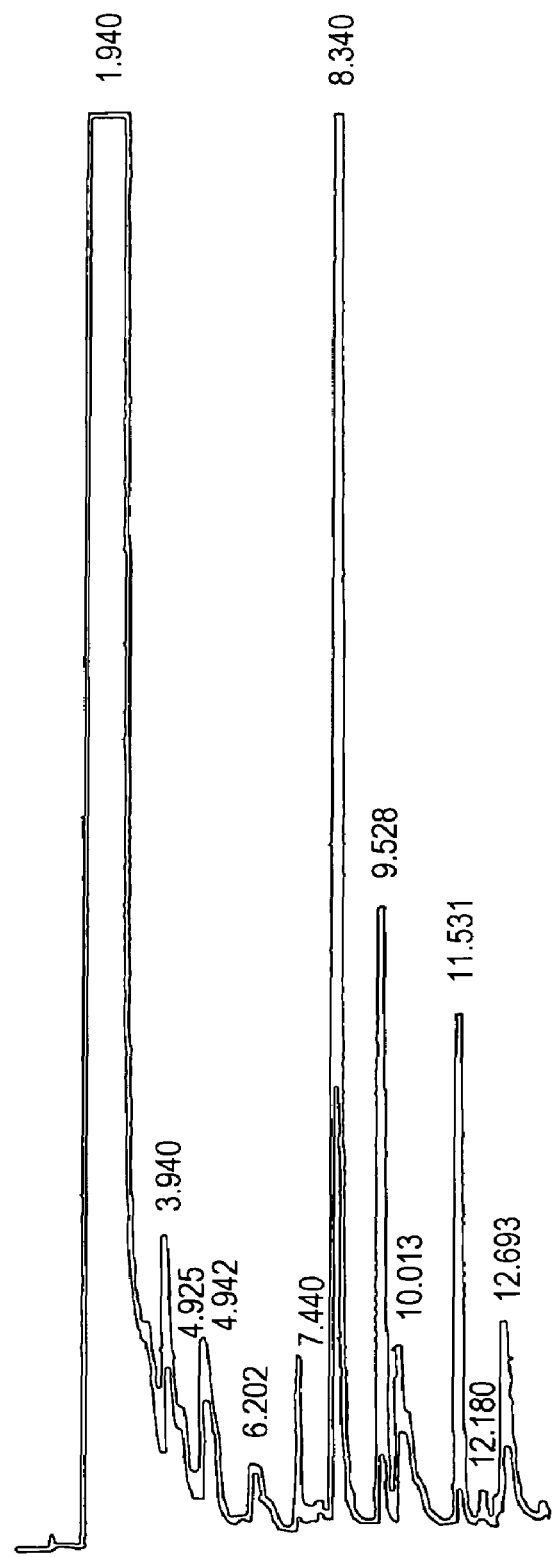

Recovery and separation of arabinose and xylose from complex carbohydrate polymers (a) Recovery of Arabinose and Xylose from Sugar Beet Pulp Sugar beet pulp pellets (500 g) were heated in a steam chamber in 3.5 liters of water containing 200 ml concentrated hydrochloric acid for 3 hrs. The mixture was then cooled and strained through cheese cloth to give 3.5 liters of a dark brown solution. 800 ml of this filtrate was concentrated to a syrup and treated with 500 ml acetone, 80 ml dimethoxypropane and 2 ml sulfuric acid. The mixture was stirred at room temperature for 14 hours and then stirred with log solid potassium carbonate for 2 hours. It was then poured into 400 ml ice water and extracted with hexane (1.6 liters) to give a mixture of 1,2-3,4-di-O-isopropylidene-L-arabinopyranose and 1,2-3,5-di-O-isopropylidene-D-xylofuranose. The GC profile (FIG. 16) indicated that 1,2-3,4-di-O-isopropylidene-L-arabinopyranose was the major pentose sugar recovered and that much smaller amounts of 1,2-3,5-di-O-isopropylidene-D-xylofuranose were also recovered. The compounds are separated as in the previous Examples.

Example 10

(b) Recovery of Arabinose and Xylose from Gum Ghatti

Figure 17:
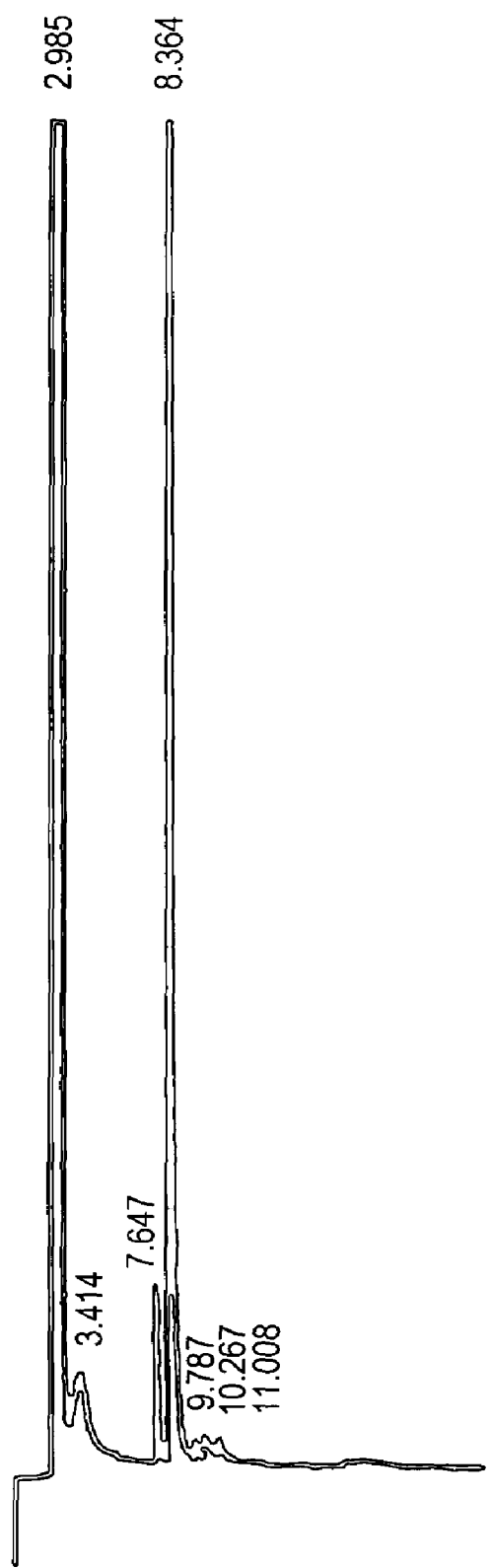

Hydrolysis and treatment of gum ghatti under the conditions described for sugar beet in 7(a) above led to good recovery of 1,2-3,4-di-O-isopropylidene-L-arabinopyranose as indicated in the gas chromatograph in FIG. 17.

Example 11

(c) Recovery of Arabinose and Xylose from Gum Arabic

Figure 18:
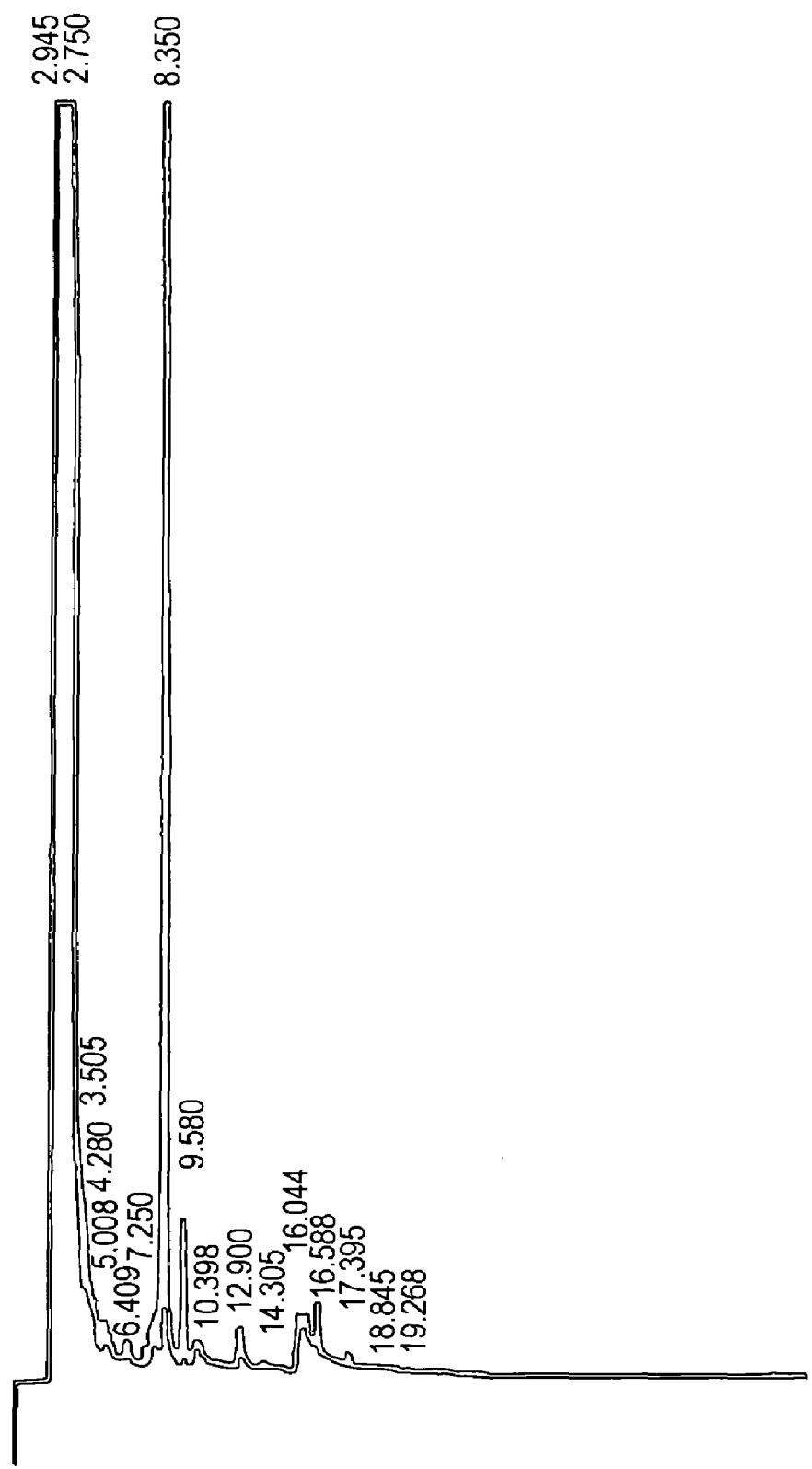

Hydrolysis and treatment of gum arabic under the conditions described for sugar beet in 7(a) above led to good recovery of 1,2-3,4-di-O-isopropylidene-L-arabinopyranose as indicated in the gas chromatograph in FIG. 18.

The process of the present invention provides for separation of the acetals by solvent extraction. Distillation, particularly vacuum distillation, or chromatography can be used but are more time consuming and expensive.

It is intended that the foregoing description be only illustrative of the present invention and that the present invention be limited only by the hereinafter appended claims.

I claim:

1. A process for the separation of arabinose and xylose acetals which comprises:
   (a) providing a mixture comprising xylose and arabinose;
   (b) reacting the mixture with a ketone or aldehyde so as to form a mixture of xylose monoacetal and arabinose diacetal; and
   (c) separating the arabinose diacetal and xylose monoacetal from the reaction mixture by a polar solvent and non-polar solvent extraction so that there is a phase separation with the of xylose monoacetal in the polar solvent and the diacetal arabinose in the non-polar organic solvent.

2. The process of claim 1 wherein the mixture in step (a) is from a hydrolysate of corn fiber or sugar beet pulp.

3. The process of claim 1 wherein the xylose monoacetal is extracted from the mixture in step (c) with an acid in water as the polar solvent for the xylose monoacetal and the arabinose diacetal by the non-polar solvent, so that there is a phase separation.

4. The process of any one of claims 1, 2, or 3 wherein the arabinose diacetal and xylose monoacetal which are separated in step (c) are pure isomers.

5. A process for the separation of arabinose diacetal and xylose monoacetal from a mixture comprised of saccharides which comprises:
   (a) reacting the mixture with a ketone or an aldehyde so as to form the arabinose diacetal and xylose monoacetal;
   (b) concentrating the mixture to a syrup;
   (c) extracting the syrup with a non-polar organic solvent in which the acetals of arabinose diacetal and xylose monoacetal are soluble to provide the arabinose diacetal and xylose monoacetal in the organic solvent;
   (d) separating the arabinose diacetal and xylose monoacetal from the organic solvent; and
   (e) separating the arabinose diacetal from the xylose monoacetal by a polar solvent and a non-polar solvent extraction, so that there is a phase separation with the xylose monoacetal in the polar solvent and the arabinose diacetal in the non-polar organic solvent.

6. The process of claim 5 wherein the mixture of step (a) is a syrup from a hydrolysate of corn fiber or sugar beet pulp.

7. The process of claim 5 or 6 wherein xylose monoacetal is extracted from the mixture with water or a polar organic solvent as the polar solvent and then separated from the water or the polar organic solvent.

8. The process of claim 5 or 6 wherein in addition after step (e) the xylose monoacetal and arabinose diacetal are separately hydrolyzed to form xylose and arabinose.

9. The process of claim 5 or 6 wherein in step (e) the arabinose diacetal and the xylose monoacetal which are separated are pure isomers.

10. The process of claims 1, 2, 4 or 3 wherein the mixture of saccharides in step (a) is produced by enzyme or acid hydrolysis of saccharides.

* * * * *

UNITED STATES PATENT AND TRADEMARK OFFICE
CERTIFICATE OF CORRECTION

PATENT NO. : 7,498,430 B2
APPLICATION NO. : 10/984529
DATED : March 3, 2009
INVENTOR(S) : Rawle I. Hollingsworth It is certified that error appears in the above-identified patent and that said Letters Patent is hereby corrected as shown below:

Column 2, line 57, "a five 95)" should be --a five (5)--.

Column 3, line 11, "1,2-3,4-diO-isopropylideneL-arabinopyranose" should be --1,2-3,4-di-O-isopropylidene-L-arabinopyranose--.

Column 3, line 23, "Ge" should be --GC--.

Column 3, line 54, remove "1" at the end of the paragraph.

Column 6, line 39, "log" should be --10 g--.

Column 7, line 16, "with the of xylose" should be --with the xylose--.

Column 8, line 27, "claims 1,2,4 or 3" should be --claims 1,2 or 3--.

Signed and Sealed this

Twenty-fifth Day of August, 2009

David J. Kappos
*Director of the United States Patent and Trademark Office*